United States Patent [19]

Furkert

[11] 4,049,646
[45] * Sept. 20, 1977

[54] PROCESS FOR THE MANUFACTURE OF LACTAMS

[75] Inventor: Herbert Furkert, Grosskonigsdorf, Germany

[73] Assignee: Davy Powergas GmbH, Cologne, Germany

[*] Notice: The portion of the term of this patent subsequent to Sept. 25, 1990, has been disclaimed.

[21] Appl. No.: 261,220

[22] Filed: June 9, 1972

[30] Foreign Application Priority Data

June 18, 1971 Germany .............................. 2130037

[51] Int. Cl.$^2$ ........................................ C07D 201/04
[52] U.S. Cl. ........................... 260/239.3 A; 423/356; 423/387; 423/525; 423/530; 423/541 A
[58] Field of Search ................ 260/239.3 A; 423/356, 423/387, 525, 530, 541

[56] References Cited

U.S. PATENT DOCUMENTS

| 2,221,369 | 11/1940 | Cass | 260/239.3 A |
| 3,133,055 | 5/1964 | Grulet et al. | 260/239.3 A |
| 3,275,407 | 10/1966 | Furkert et al. | 423/356 |
| 3,292,996 | 12/1966 | Furkert et al. | 423/356 |
| 3,321,275 | 5/1967 | Furkert et al. | 423/356 |
| 3,359,069 | 12/1967 | Furkert et al. | 423/541 |
| 3,383,170 | 5/1968 | Furkert et al. | 423/541 |
| 3,701,809 | 10/1972 | DeRooij et al. | 423/387 |
| 3,761,575 | 10/1973 | Furkert | 423/356 |
| 3,852,272 | 12/1974 | DeRooij | 260/239.3 A |
| 3,852,273 | 12/1974 | DeRooij | 260/239.3 A |

OTHER PUBLICATIONS

Sittig "Caprolactam and Higher Lactams" (Noyes Development Corp.), p. 70 (1966).
Seel "Fortschr. Chem. Forsch." vol. 4, pp. 301–332, (1963).

Primary Examiner—Henry R. Jiles
Assistant Examiner—Robert T. Bond
Attorney, Agent, or Firm—Millen & White

[57] ABSTRACT

In a process for manufacturing a lactam which includes rearranging a cycloalkanone-oxime with sulfuric acid to form said lactam, neutralizing the rearrangement mixture with ammonia to form ammonium sulfate, and separating said lactam and said ammonium sulfate, the improvement which comprises:
   a. forming the ammonium sulfate into finely divided particles;
   b. burning the particles at a temperature of 850° – 1250° C. to form an $SO_2$-containing gas;
   c. oxidizing the $SO_2$-containing gas to form sulfuric acid; and
   d. recycling at least a portion of the sulfuric acid to the cycloalkanone-oxime rearrangement step.

No external source of sulfuric acid is required. A portion of the $SO_2$-containing gas can be used for the manufacture of hydroxylamine sulfate, in which case no external source of $SO_2$ need be required.

17 Claims, 1 Drawing Figure

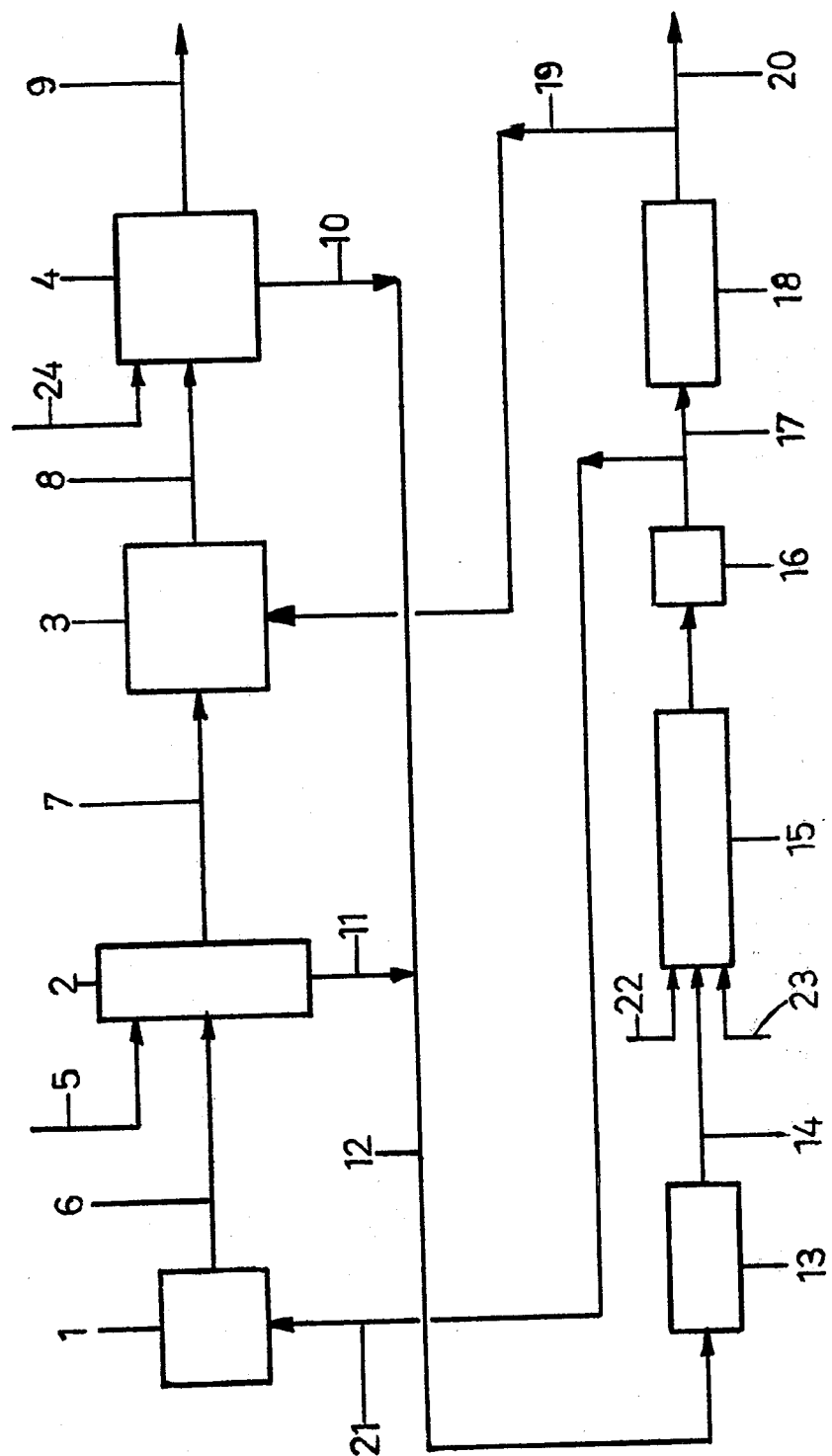

PROCESS FOR THE MANUFACTURE OF LACTAMS

CROSS-REFERENCE TO RELATED APPLICATION

Details of a process for the combustion of ammonium sulfate are described in copending, commonly assigned U.S. patent application Ser. No. 228,258, filed Feb. 22, 1972 now U.S. Pat. No. 3,795,731.

DESCRIPTION OF THE INVENTION

1. Field of the Invention

This invention relates to a process for manufacturing lactams from cycloalkanone-oximes.

2. Description of the Prior Art

Several processes are known by which lactams may be prepared from cycloalkanone-oximes. The cycloalkanone-oximes can be prepared by reacting a cycloalkanone with hydroxylamine sulfate solution and neutralizing the sulfuric acid thusly liberated with ammonia. In general, the manufacture of lactams involves a ring expansion via Beckmann rearrangement of cyclic ketoximes. Several basic processes for manufacturing lactams are known including the hydrogenation of phenol to cyclohexanole and dehydrogenation of cyclohexanole to cyclohexanone and reaction of the cyclohexanone with hydroylamine sulfate solution to form cyclohexanone oxime, followed by Beckmann rearrangement with sulfuric acid; the catalytic oxidation of cyclohexane to cyclohexanone, followed by reaction with hydroylamine sulfate solution to form cyclohexanone oxime, and then Beckmann rearrangement by sulfuric acid; and the light catalyzed reaction of cyclohexane with nitrosyl chloride to cyclohexanone oxime hydrochloride, followed by a Beckmann rearrangement. These processes, described with particular reference to the manufacture of caprolactam, are also applicable to the manufacture of other lactams.

The manufacture of lactams by a process which includes neutralizing a reaction mixture containing sulfuric acid with ammonia to form ammonia sulfate, such as the manufacture of ε-caprolactam via cyclohexanone-oxime, is coupled with the unavoidable production of about 1 to 4 tons ammonium sulfate per ton of caprolactam, depending on the particular process used. The ammonium sulfate has an unfavorable effect on the economics of manufacturing the lactam since there is very little demand for this by-product. Using the ammonium sulfate directly as a fertilizer is not feasible because the impurities it contains result in a colored product which crystallizes poorly.

Accordingly, the prior art has proposed various techniques to improve the economics of lactam production. It is known, before crystallization, to subject the ammonium sulfate solution arising in the manufacture of caprolactam to a heat treatment under pressure in order to manufacture a fertilizer (German Published Specification No. 1,284,954) or to treat the solution with aluminum sulfate and the sodium salt of ethylenediaminetetraacetic acid (Italian Patent Specification No. 678,180). Ammonium sulfate solutions from the manufacture of caprolactam, which are rich in organic constituents, can, according to Netherlands Patent Applications Nos. 65-16,058 and 65-16,059, be evaporated and thereby separated from the organic constituents, and then crystallized. While these and other prior art measures improve the quality of the ammonium sulfate produced, they are not economically satisfactory because the demand for ammonium sulfate as a fertilizer is very restricted.

From the teachings of German Published Specification No. 1,916,149 it is possible to neutralize the rearrangement reaction mixture obtained in lactam manufacture with calcium oxide, magnesium oxide, zinc oxide or copper oxide instead of ammonia, and to split the resultant metal sulfates under reductive conditions to form the metal oxides and sulfur dioxide. The metal oxide is reused for neutralization, and the sulfur dioxide converted into sulfuric acid which is employed in the rearrangement reaction. This process suffers from the disadvantages that neutralization with metal oxides takes place more slowly than with the more extensively used ammonia, and that contamination of the metal oxide recycled to the neutralization occasioned by the reductive splitting of the sulfate is frequently unavoidable.

OBJECTS OF THE INVENTION

Accordingly, it is an object of the present invention to provide a process for the manufacture of lactams which eliminates the buildup of ammonium sulfate by-product.

Another object of this invention is to provide a process for the manufacture of hydroxylamine sulfate which eliminates the buildup of ammonium sulfate by-product.

An additional object of this invention is to provide a process for internally generating sulfuric acid required in lactam production.

A further object of this invention is to provide a process for internally generating sulfur dioxide required in hydroxylamine sulfate production.

Yet another object of this invention is to provide a process for lactam production in which the thermal efficiency of the reaction is greatly improved.

A more specific object of the present invention is to provide a process for the production of ε-caprolactam.

Upon further study of the specification and appended claims, further objects and advantages of this invention will become apparent.

SUMMARY OF THE INVENTION

The present invention provides, in a process for manufacturing a lactam which includes rearranging a cycloalkanone-oxime with sulfuric acid to form said lactam, neutralizing the rearrangement mixture with ammonia to form ammonium sulfate, and separating said lactam and said ammonium sulfate, the improvement which comprises:
  a. forming the ammonium sulfate into finely divided particles;
  b. burning the particles at a temperature of 850° – 1250° C. to form an $SO_2$-containing gas;
  c. oxidizing the $SO_2$-containing gas to form sulfuric acid; and
  d. recycling at least a portion of the sulfuric acid to the cycloalkanone-oxime rearrangement step.

A portion of the $SO_2$-containing gas can be used for the manufacture of hydroxylamine sulfate. No external source of sulfuric acid is required.

BRIEF DESCRIPTION OF THE DRAWING

The above and other objects of the invention will become more fully apparent to those skilled in the art from the following detailed discussion, taken with the annexed drawing, which schematically illustrates a plant suitable for carrying out the process of this invention.

DETAILED DISCUSSION

The invention provides a process for the manufacture of lactams from cycloalkanone-oximes by rearrangement with sulfuric acid or oleum, neutralization of the mixture from the rearrangement reaction will ammonia and separation of the lactam from the ammonium sulfate formed, in which the ammonium sulfate is incorporated into the process of lactam manufacture so that there is no longer a problem of purification or sale of this byproduct. The economics of lactam production are greatly improved by recoveri g the sulfuric acid required for the Beckmann rearrangement from the ammonium sulfate which is formed.

According to the invention, this is achieved by burning the ammonium sulfate by-product formed in a solid, finely divided form, at temperatures between 850°–1250° C., to form an $SO_2$-containing gas, reacting the gas by a known $SO_2$ oxidation at temperatures between 400°–600° C. followed by absorption to give sulfuric acid or oleum, and recycling the sulfuric acid or the oleum to the rearrangement stage. Any ammonium sulfate or ammonia and ammonium bisulfate which may be transiently formed in the combustion furnace burns completely to sulfur dioxide, water vapor and nitrogen, without forming significant amounts of nitrogen oxides. The combustion gas, which contains, for example, 5–7% by volume of $SO_2$, is preferably reacted in a multi-stage contact plant using a catalyst containing $V_2O_5$, with cooling of the reaction gas between the contact stages, to give $SO_3$ which is then absorbed to form sulfuric acid or oleum. The sulfuric acid or oleum recycled to the rearrangement stage provides the entire sulfuric acid or oleum requirement of the process.

In most processes for the manufacture of lactams, the ammonium sulfate is obtained as an aqueous solution containing between 35–46% by weight, preferably between 36–41% by weight, ammonium sulfate. This solution is advisably partially or wholly evaporated prior to combustion, whereupon solid ammonium sulfate crystallizes out. The mother liquor which remains behind is then recycled to the neutralization stage.

In accordance with a preferred embodiment of this invention, ammonium sulfate is ground to an average particle size of between 0.01 and 1.0 mm., preferably between 0.01 and 0.5 mm., and especially between 0.02 and 0.2 mm. average diameter. By average particle size as used herein is meant a particle size such that 90% will pass through a screen of this size. Such a fine comminution makes it possible to feed ammonium sulfate uniformly into the combustion hamber and also to effect rapid combustion of the indi lual sulfate particles. The use of particles smaller than about 0.01 mm. diameter results in handling difficulties, while the use of particles larger than about 1.0 mm. in diameter leads to incomplete combustion at temperatures suitable for decomposing ammonium sulfate without the formation of nitrogen oxides or ammonia.

The ammonium sulfate is preferably burned at a temperature of between 950°–1150° C. In this temperature range, combustion proceeds in such a manner that neither ammonia nor nitrogen oxides occur in the combustion gas in a pronounced quantity, i.e., generally less than 200 ppm. ammonia and less than 40 ppm. nitrogen oxides are produced. Preferably, an $O_2$ concentration of between 1 and 8% by volume inclusive, especially 1.8 to 4.5% by volume inclusive, is maintained in the gases discharged from the combustion chamber, corresponding to from 1.13 to 3.61 times the stoichiometric amount of oxygen required for complete fuel methane combustion within the combustion chamber. By operating in this manner, the necessity of purifying sulfuric acid or oleum before recycling it to the Beckmann rearrangement is avoided.

Typically, combustion chamber residence times for the particulate ammonium sulfate range from 0.3 to 15 sec., preferably from 0.4 to 2.5 sec.

In a preferred embodiment of this invention, particulate ammonium sulfate is blown into the combustion chamber by means of a carrier gas stream, such as air, nitrogen, fuel gases, natural gas or carbon monoxide.

In using a cylindrical combustion chamber, for example, the ammonium sulfate is preferably injected axially from an end face, whereas the burners are arranged in the cylindrical shell and oriented radially or tangentially into the combustion chamber. Feeding a particulate ammonium sulfate stream by blowing is likewise possible from the ceiling in an upright combustion furnace, and from an end face in case of a horizontal furnace. It is, of course, also possible to orient the ammonium sulfate feed point and the burners in some other mutual relationship, the only requirement for finite operability being that the particulate ammonium sulfate stream enters into the combustion zone of the furnace.

Preferably, the ammonium sulfate is blown into the combustion chamber of a standard size furnace with a carrier gas comprising about 0.1 to 0.5 $Nm^3$ of a carrier gas, such as air, per kg. of ammonium sulfate. This ratio ensures a uniform feed of the sulfate into the combustion zone without allowing an unnecessarily large amount of air to enter into the combustion chamber as the carrier gas. The air actually utilized for combustion is introduced separately at the burners. In order to precisely guide the ammonium sulfate particle stream into the combustion zone, it is preferred to feed the finely divided ammonium sulfate to the flame through a lance extending into the combustion chamber. The lance is a straight pipe consisting of quartz or stainless steel. It extends through an opening provided in the furnace ceiling and is connected to a fan by means of a pipeline which has attached thereto a dosing apparatus for the ammonium sulfate.

The lance can be introduced into the combustion chamber to a varying extend corresponding to its scattering range, so that the entire combustion zone is charged uniformly with ammonium sulfate. It is advantageous to cool the lance in order to prevent the premature splitting off of ammonia, such as by air or cooling liquid which is circulated around the lance outside the furnace.

The air jet for conveying particulate ammonium sulfate into the combustion zone can be preheated to improve thermal efficiency as well as to render the feed of sulfate uniform; however, a sufficient temperature differential must be maintained with respect to the decomposition temperature range of the ammonium sulfate (240° to 270° C). In general, the stream of conveying air will preferably be preheated to a temperature of not more than 200° C., preferably in the range of 50° to 150° C.

According to a preferred embodiment of the invention, sulfur is simultaneously burned in the combustion chamber. In this embodiment, the $SO_2$ content of the combustion gas is increased, thereby compensating for sulfur losses elsewhere. A fuel oil rich in sulfur is advantageously employed as the carbonaceous fuel, in order to obtain a combustion gas having an $SO_2$ content sufficient for subsequent contact catalysis, e.g., 5 to 7% by volume $SO_2$. Other sulfur-containing waste products, such as, for example, by-product sulfuric acids containing organic compounds and/or ammonium compounds of the type disclosed in U.S. Pat. No. 3,359,069, can also be burned simultaneously.

The ammonium sulfate is preferably burnt using a fuel containing carbon and/or sulfur. In doing so, the ammonium ion or the transiently formed ammonia is oxidized to nitrogen and water vapor without nitric oxides being formed in objectionable concentration during the combustion. If the concentration of nitric oxide in the combustion gas becomes so great that the sulfuric acid or oleum produced also contains nitric oxide, this acid can be purified, either before recycling to the rearrangement reaction stage or during the rearrangement reaction, by reaction with a little ammonium sulfate, amidosulfonic acid, urea or the like. Simultaneously with the ammonium oxidation, the sulfate is reduced to sulfur dioxide, giving a combustion gas which contains, e.g., 5 to 7% by volume of $SO_2$. Heavy oil or natural gas can be used as the fuel and these can also contain sulfur. The conjoint combustion or sole combustion of hydrogen sulfide or of sulfur can also be used if an amount of sulfuric acid in excess of that required for production of the lactam is required.

While the process of this invention can be conducted batchwise or discontinuously, best results are generally attained when it is operated as a continuous process. While actual yields will, of course, vary, in theory each mole of ammonium sulfate is decomposed to one mole of sulfur dioxide, which is then converted to one mole of sulfuric acid. Additional sulfur dioxide can be formed during combustion of a sulfur-containing fuel, e.g., fuel oil containing 0.5 to 2.0 wt.% sulfur. It an excess of sulfuric acid beyond that which is required for the Beckmann rearrangement is generated, this can be drawn off as a separate by-product or the formation of sulfuric acid can be decreased by decreasing the sulfur content of the combustion fuel. Preferably, however, at least a portion of the $SO_2$ containing gas obtained from the combustion chamber is fed to a process for preparing hydroxylamine sulfate by reacting sulfur dioxide with a solution of ammonium nitrite and ammonium bicarbonate or with a solution of ammonium nitrite and ammonium bisulfite at a temperature of approx. 0° C and subsequently hydrolyzing the obtained disulfonate to hydroxylamine sulfate.

If ammonium sulfate which arises in the oxime-forming stage is co-processed in accordance with the invention, an appropriate proportion of the combustion gas containing $SO_2$, e.g., 15 to 40 vol. % of a gas containing 5 – 7 vol. % $SO_2$, is available for the manufacture of hydroxylamine sulfate $(NH_2OH)_2$—$H_2SO_4$.

One suitable technique for preparing hydroxylamine sulfate is the classical Raschig process, described in Kirk-Othmer, Vol. 7 (1951), page 766, paragraph 4, Briefly, the classical Raschig process involves the reduction of sodium nitrite with sodium bisulfite and sulfur dioxide to give sodium hydroxylamine -N, N-disulfonate, followed by hydrolysis of the hot solution to give hydroxylammonium acid sulfate.

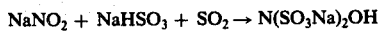

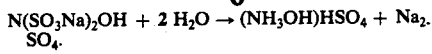

The modified Raschig process using ammonium salts as mentioned above instead of sodium salts requires also sulfur dioxide. The modern process of preparing hydroxylamine sulfate by catalytic hydrogenation of nitrogen oxide has need of sulfuric acid. Our process allows to make available the sulfur component for all of these processes.

The amount of sulfur dioxide formed by the combustion of ammonium sulfate will vary under otherwise identical conditions with the amount of sulfur burned in the fuel. Preferably the fuel will contain at least 0.1 to 0.5 wt. % sulfur in order to form sufficient $SO_2$ during combustion to make up for losses elsewhere in the system. When all of the $SO_2$ is converted directly to sulfuric acid or oleum, from 60 to 100 wt. % of this sulfuric acid is recycled to the Beckmann rearrangement stage, and 0 to 40 wt. % of this sulfuric acid can be drawn off as a by-product. If the combustion fuel is low in sulfur, e.g., contains below 0.1 wt. % sulfur, it will generally be desirable to recycle the total sulfuric acid output to the Beckmann rearrangement stage.

When a portion of the $SO_2$-containing gas is used in the manufacture of hydroxylamine sulfate, generally about 15 to 40 mol. %, of this gas, e.g., having an $SO_2$ content of 5-7 mol. %, is fed to the hydroxylamine plant, and the remaining 60 to 85 mol % is fed to a sulfuric acid plant. Of course, the yield of sulfuric acid based on $SO_2$ in the combustion gas is reduced by feeding only a portion of the $SO_2$-containing gas to the sulfuric acid plant, and a slightly higher sulfur content in the combustion fuel, e.g., at least 0.5 to 2.0 wt. % sulfur, will generally be required to produce an excess of sulfuric acid beyond that required for the Beckmann rearrangement step.

Preferably, ammonium sulfate which arises during the oximation of cyclohexanone and/or during the rearrangement of cyclohexanone-oxime is used in accordance with the process of the invention. The process of the invention is applicable to all caprolactam manufacturing processes which involve the Beckmann rearrangement of cyclohexanone-oxime, that is to say also the photochemical formation of oxime from cyclohexane and nitrosyl chloride, and to the manufacture of other lactams, such as, for example, capryllactam and lauryllactam via the corresponding oximes.

The present invention further provides that the heat of the gas produced during the combustion is utilized in a heat exchanger, especially a waste heat boiler, in the course of which the gas cools to between 260° and 420° C. The steam generated in the waste heat boiler can be utilized for the evaporation of the ammonium sulfate solution and/or for melting the oxime. It is also possible to pre-warm the feed air and the combustion air by means of the waste heat.

Referring now to the Drawing, in oximation reactor 2, cyclohexanone arriving through pipeline 5 and hydroxylamine sulfate supplied from Raschig plant 1 through pipeline 6 are reacted, and the liberated sulfuric acid is neutralized with ammonia. The oxime is separated from the ammonium sulfate solution formed and is passed through pipeline 7 to rearrangement reactor 3. In reactor 3, the cyclohexanone-oxime is rearranged to ε-caprolactam by means of concentrated sulfuric acid fed through pipeline 19. The mixture from the rearrangement reaction passes through pipeline 8 into neutralization reactor 4 where it is neutralized by gaseous ammonia supplied through pipeline 24. In a conventional separation apparatus (not shown), the mixture is separated into ammonium sulfate solution and ε-caprolactam which flows through pipeline 9 into a purification plant (not shown). The ammonium sulfate solution which forms is passed through pipeline 10, together with the ammonium sulfate solution coming through pipeline 11 from the oximation stage 2, to evaporator 13 by means of pipeline 12, and ammonium sulfate crystallizes out in the evaporator.

Solid ammonium sulfate is introduced pneumatically, through pipeline 14, into combustion furnace 15 where it is burnt with air from line 23 and a sulfur-containing fuel oil, or sulfur from line 22. The combustion gas containing $SO_2$ leaves furnace 15 at about 1100° C. and transfers its heat to subsequent waste heat boiler 16, while being cooled to about 400° C. After conventional purification and drying (not shown), at least a portion of the gas is then passed via line 17 to a sulfuric acid contact plant 18. The concentrated sulfuric acid produced therein partly returns through pipeline 19 to the rearrangement stage 3 of the manufacture of caprolactam and is partly tapped off via line 20 for other purposes.

At line 17 a portion of the dry and purified $SO_2$-containing gas is branched off and passed through pipeline 21 to hydroxylamine plant 1. The entire $SO_2$ consumption of the hydroxylamine plant can be supplied by burning additional sulfur or hydrogen sulfide and/or a fuel of sufficient S-content in furnace 15.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsever.

EXAMPLE 129 kg/hour of hydroxylamine sulfate in an aqueous solution is reacted with 159 kg/hour of cyclohexanone at 40–50° C, with vigorous stirring, to form 165 kg/hour of cyclohexanone-oxime. During the reaction, 89.1 kg/hour of 30% aqueous ammonia is introduced into the mixture, while cooling. After separating off the cyclohexanone-oxime, 103.7 kg/hour of ammonium sulfate in a concentrated aqueous solution is left.

The 165 kg/hour of cyclohexanone-oxime is rearranged by adding 214 kg/hour of 100% sulfuric acid at about 110°–120° C, with stirring, to give ε-caprolactam; this requires intensive cooling. The mixture from the rearrangement reaction is then transferred to a neutralization vessel and neutralized at 40°–50° C by adding 74.5 kg/hour of ammonia. After separating the caprolactam layer from the aqueous ammonium sulfate solution, and after purification, ε-caprolactam is obtained at the rate of 155.1 kg/hour.

The 288.5 kg/hour of ammonium sulfate obtained from the neutralization stage, in the form of a nearly saturated aqueous solution, is combined with the 103.7 kg/hour of ammonium sulfate from the oximation stage and evaporated to obtain a crystalline form. 388 kg/hour of solid ammonium sulfate is obtained.

The 388 kg/hour of ammonium sulfate, 2.4 kg/hour of sulfur and about 44.4 kg/hour of fuel oil are burnt in a furnace kept at 1050° C by the combustion of fuel oil. The air for the combustion of the fuel oil is prewarmed to about 500° C. The fuel oil is burnt using 1.84 times the stoichiometric amount of air required for complete combustion. The ammonium sulfate is communited to an average particle size of less than 0.1 mm before introduction into the feed air stream and is metered into 2.5 kg per $Nm^3$ of feed air, using a feed screw.

The combustion gas, which is at about 1050° C, is coprocessed in an existing sulfuric acid plant. It passes through a waste heat boiler in which about 1.12 tons of steam (55 atmosphere gauge) is generated per ton of ammonium sulfate to be processed. After passing through the waste heat boiler, the gas is cooled further, mixed with air, and dried. 1150 $Nm^3$/hour of dry gas containing about 5.9% by volume of $SO_2$ is obtained. Of this gas, 313 $Nm^3$/hour is recycled, after cooling and drying, to the manufacture of hydroxylamine sulfate. The remaining 837 $Nm^3$/hour of combustion gas is passed into the contact plant for the manufacture of sulfuric acid. 214 kg/hour of $H_2SO_4$ is manufactured therefrom which is re-employed in the rearrangement reaction of the cyclohexanone-oxime.

The preceding example can be repeated with similar success by substituting the generically or specifically described reactants and/or operating conditions of this invention for those used in the preceding example.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for manufacturing a lactam which includes rearranging a cycloalkanone-oxime with sulfuric acid or to form said lactam, completely neutralizing the rearrangement mixture with ammonia to form ammonium sulfate, and separating said lactam and said ammonium sulfate, the improvement which comprises:
    a. forming said ammonium sulfate into finely divided particles;
    b. burning said particles at a temperature of 850° – 1250° C. to form an $SO_2$-containing gas;
    c. oxidizing said $SO_2$-containing gas to form sulfuric acid; and
    d. recycling at least a portion of said sulfuric acid to the cycloalkanone-oxime rearrangement step.

2. A process according to claim 1, wherein said ammonium sulfate particles are burnt by combustion of a carbonaceous fuel.

3. A process according to claim 1, wherein said ammonium sulfate particles are burnt by combustion of a sulfur-containing fuel.

4. A process according to claim 1, wherein said ammonium sulfate is formed into solid particles having a particle size range of 0.01 – 0.5 mm. diameter.

5. A process according to claim 4, wherein said particles are fed into a combustion chamber by means of a carrier gas stream.

6. A process according to claim 5, wherein said carrier gas is preheated to a temperature of less than 200° C.

7. A process according to claim 5, wherein said particles are blown into said combustion chamber with 0.1–0.5 $Nm^2$ of carrier gas per kg. of ammonium sulfate.

8. A process according to claim 1, wherein said lactam is ε-caprolactam.

9. A process according to claim 1, wherein the heat of the gas produced in the combustion stage is heat exchanged to evaporate ammonium sulfate solution.

10. A process according to claim 1, wherein the heat of gas produced in the combustion stage is heat exchanged to preheat said carrier gas.

11. A process according to claim 1, wherein the heat of the gas produced in the combustion stage is heat exchanged to fuse said oxime.

12. A process according to claim 1, wherein the portion of sulfuric acid recycled is sufficient to provide substantially all of the sulfuric acid required for the Beckmann rearrangement step.

13. A process according to claim 1, further including feeding at least a portion of said $SO_2$-containing gas to a process for the manufacture of hydroxylamine sulfate, and reacting resultant hydroxylamine sulfate with cycloalkanone to form said cycloalkanone-oxime and additional ammonium sulfate.

14. A process according to claim 13, further including recovering ammonium sulfate from said process and adding said ammonium sulfate to the ammonium sulfate obtained in the lactam manufacturing process.

15. A process according to claim 13, wherein the portion of $SO_2$-containing gas is sufficient to provide substantially all of the $SO_2$ required for the production of said hydroxylamine sulfate.

16. A process according to claim 5, wherein the finely divided ammonium sulphate is fed to the flame through a lance which opens into the combustion chamber.

17. A process according to claim 1, wherein the ammonium sulphate is burnt at a temperature of from 950° to 1,150° C. and that an oxygen concentration of from 1 to 8% by volume, is maintained in the gases leaving the combustion chamber.

* * * * *

UNITED STATES PATENT AND TRADEMARK OFFICE
CERTIFICATE OF CORRECTION

PATENT NO. : 4,049,646
DATED : September 20, 1977
INVENTOR(S) : HERBERT FURKERT

It is certified that error appears in the above–identified patent and that said Letters Patent are hereby corrected as shown below:

Claim 1, Column 8, line 36: After "acid or", insert

-- oleum -- .

Signed and Sealed this

Thirty-first Day of January 1978

[SEAL]

Attest:

RUTH C. MASON
*Attesting Officer*

LUTRELLE F. PARKER
*Acting Commissioner of Patents and Trademarks*